United States Patent
Mathis et al.

(10) Patent No.: US 6,221,029 B1
(45) Date of Patent: Apr. 24, 2001

(54) UNIVERSAL BIOPSY SYSTEM

(75) Inventors: John M. Mathis, Roanoke, VA (US); Stephen M. Belkoff, Kingsville; Charles J. Phillips, Annapolis, both of MD (US); Marshall D. Welch, III, Lafayette, CO (US); Steven M. Kmiec, Coventry, CT (US)

(73) Assignee: Stryker Corporation, Kalamazoo, MI (US)

(*) Notice: Subject to any disclaimer, the term of this patent is extended or adjusted under 35 U.S.C. 154(b) by 0 days.

(21) Appl. No.: 09/311,692

(22) Filed: May 13, 1999

(51) Int. Cl.$^7$ .................................................. A61B 10/00
(52) U.S. Cl. ........................ 600/564; 600/567; 606/167; 604/22
(58) Field of Search .................................. 600/562, 564, 600/567; 606/167, 170, 184, 185; 604/22

(56) References Cited

U.S. PATENT DOCUMENTS

| | | | |
|---|---|---|---|
| 3,949,747 | 4/1976 | Hevesy | 128/28 |
| 4,256,119 | 3/1981 | Gauthier | 128/754 |
| 4,262,676 | 4/1981 | Jamshidi | 128/753 |
| 4,266,555 | 5/1981 | Jamshidi | 128/753 |
| 4,356,828 | 11/1982 | Jamshidi | 128/754 |
| 4,513,754 | 4/1985 | Lee | 128/753 |
| 4,609,370 * | 9/1986 | Morrison | 600/567 |
| 4,793,363 | 12/1988 | Ausherman et al. | 128/754 |
| 4,922,602 | 5/1990 | Mehl | 29/460 |
| 5,036,860 | 8/1991 | Leigh et al. | 128/754 |
| 5,090,419 * | 2/1992 | Palestrant | 600/567 |
| 5,127,419 | 7/1992 | Kaldany | 128/754 |
| 5,186,197 | 2/1993 | Lavine | 135/25.4 |
| 5,257,632 | 11/1993 | Turkel et al. | 128/754 |
| 5,331,972 | 7/1994 | Wadhwani et al. | 128/754 |
| 5,385,151 | 1/1995 | Scarfone et al. | 128/754 |
| 5,429,138 | 7/1995 | Jamshidi | 128/753 |
| 5,476,102 | 12/1995 | Como et al. | 128/754 |
| 5,526,821 | 6/1996 | Jamshidi | 128/753 |
| 5,538,009 | 7/1996 | Byrne et al. | 128/754 |
| 5,634,473 | 6/1997 | Goldenberg et al. | 128/754 |
| 5,752,923 | 5/1998 | Terwilliger | 600/562 |
| 5,758,655 | 6/1998 | Rodriguez et al. | 128/749 |
| 5,807,275 | 9/1998 | Jamshidi | 600/567 |
| 5,807,277 | 9/1998 | Swaim | 600/567 |
| 5,843,001 * | 12/1998 | Goldenberg | 600/567 |
| 5,871,471 * | 2/1999 | Ryan et al. | 604/167 |
| 5,948,008 * | 9/1999 | Daikuzono | 606/15 |
| 6,015,391 * | 1/2000 | Rishton et al. | 600/567 |
| 6,033,369 * | 3/2000 | Goldenberg | 600/567 |

FOREIGN PATENT DOCUMENTS

255278 A1 * 3/1988 (DE) ................................. 600/567

OTHER PUBLICATIONS

Becton, Dickinson & Co., "Biopsy Needle & Instruments for Advanced Techniques", Oct. 1974.*

Procedure description for Bone Marrow Biopsy/Aspiration Diamond Cut Needle, Medical Biopsy, Inc.

Advertised Pharmaseal Ergonomically Designed Jamshidi Bone Marrow Biopsy/Aspiration Needle, Baxter Healthcare Corp., Jun. 1994.

"Percutaneous Vertebroplasty Treatment of Steroid–Induced Osteoporotic Compression Fractures", *Arthritis & Rheumatism*, vol. 41, No. 1, Jan. 1998, pp. 171–175.

"Percutaneous Polymethylmethacrylate Vertebroplasty in the Treatment of Osteoporotic Vertebral Body Compression Fractures: Technical Aspects", *American Journal of Neuroradiology*, vol. 18, pp. 1897–1904, Nov. 1997.

* cited by examiner

*Primary Examiner*—Cary O'Connor
*Assistant Examiner*—Charles Marmor, II
(74) *Attorney, Agent, or Firm*—Rosenberg, Klein & Lee

(57) ABSTRACT

A universal biopsy system is provided for performing percutaneous medical procedures. The biopsy system includes a cannula assembly removably coupled to a handle. The releasable coupling structures of the handle and the cannula assembly allow for rotational displacement of the cannula assembly using the handle, as well as the application of an axially directed force, either toward or away from the patient.

10 Claims, 3 Drawing Sheets

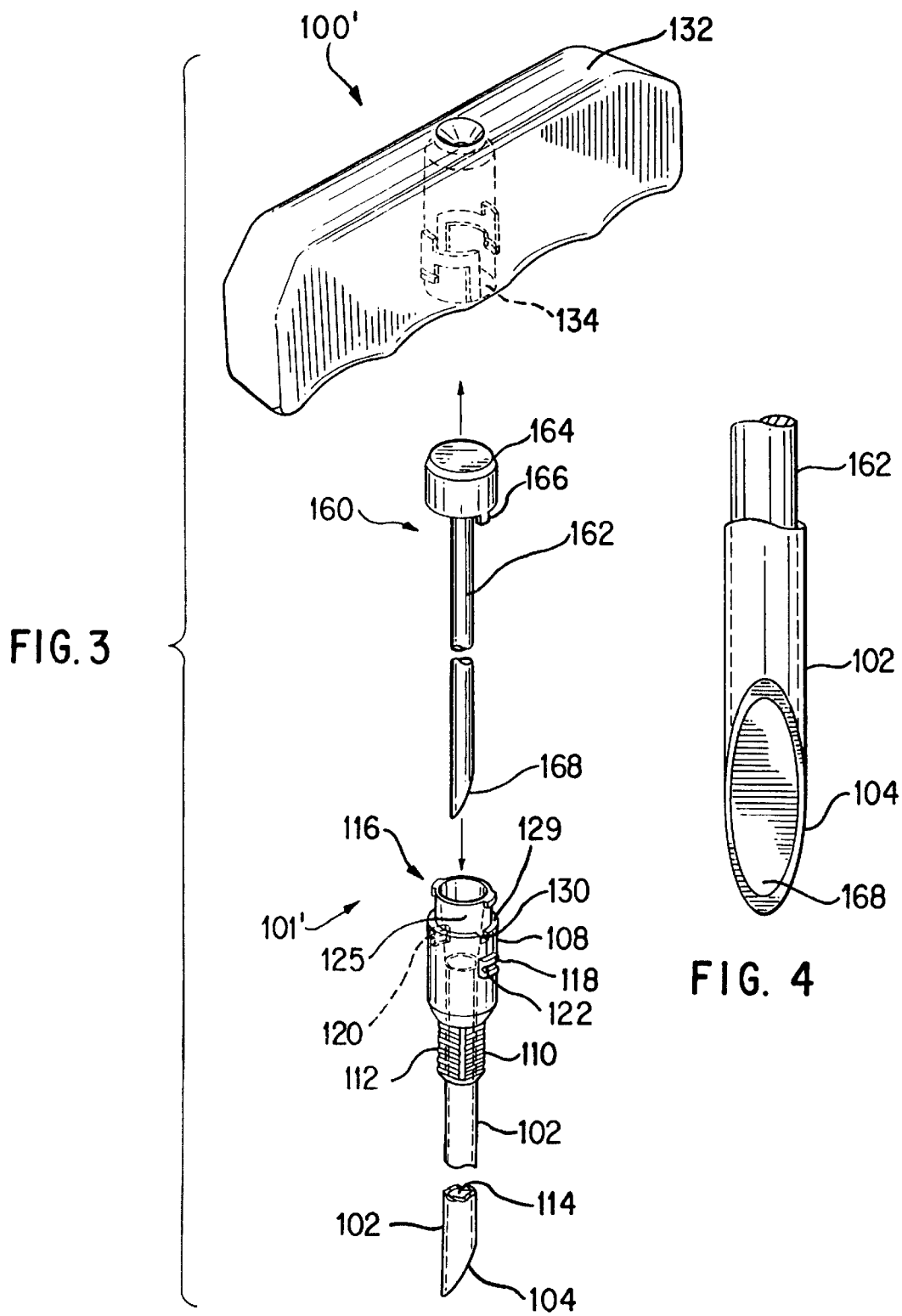

6,221,029 B1

UNIVERSAL BIOPSY SYSTEM

BACKGROUND OF THE INVENTION

1. Field of the Invention

This invention directs itself to biopsy devices utilized for percutaneous medical procedures. In particular, this invention directs itself to a biopsy system wherein a handle is releasably coupled to a cannula assembly, providing particular advantages for the performance of vertebroplasty procedures. More in particular, the handle of the present invention includes an opening formed in a lower side thereof wherein recesses are formed in opposing interior wall surfaces of the opening for receiving respective projections formed on the hub portion of the cannula. Still more in particular, this invention pertains to a biopsy system wherein the recesses formed in the opening of the handle have terminal portions in which lower and upper locking recesses are formed for rotatively and axially displacing the cannula assembly, either toward or away from patient, respectively.

2. Prior Art

Biopsy systems are well known in the art. The best prior art known to the Applicants include U.S. Pat. No. 4,922,602; U.S. Pat. No. 5,331,972; U.S. Pat. No. 5,385,151; U.S. Pat. No. 5,807,275; U.S. Pat. No. 5,752,923; U.S. Pat. No. 5,538,009; U.S. Pat. No. 5,476,102; U.S. Pat. No. 5,257,632; U.S. Pat. No. 4,256,119; U.S. Pat. No. 4,793,363; U.S. Pat. No. 5,127,419; U.S. Pat. No. 5,634,473; U.S. Pat. No. 5,758,655; U.S. Pat. No. 5,186,197; U.S. Pat. No. 4,513,754; U.S. Pat. No. 5,036,860; U.S. Pat. No. 3,949,747; U.S. Pat. No. 5,807,277; U.S. Pat. No. 5,526,821; U.S. Pat. No. 5,429,138; U.S. Pat. No. 4,356,828; U.S. Pat. No. 4,266,555; and, U.S. Pat. No. 4,262,676.

In some prior art systems the proximal end of the cannula is accessible through an opening formed in an upper side of the handle, subsequent to removal or displacement of a cover therefor. Such systems, however, do not provide a clear field of view for the physician. Other prior art systems, such as that disclosed by U.S. Pat. No. 3,949,747, have a removable handle for selective engagement with any one of a plurality of punches and probes. However, such handle is threadedly connected to the punches and probes, and therefore only capable of rotatively driving the punch or probe in a single direction, in the tightening direction of the handle, as rotation in the opposing direction will cause the handle to disengage from the selected tip.

In still other prior art systems, such as that disclosed by U.S. Pat. No. 4,513,754, the cannula is releasably held within the jaws of a collet. As the cannula is a tube, the jaw pressure thereon is limited, in order not to crush the tube, thereby limiting the axial and rotational forces which may be transferred from the handle to the cannula.

Such deficiencies are overcome by the structure of the invention of the subject Patent Application, by virtue of the removable handle that is capable of rotating a cannula assembly in either a clockwise or a counterclockwise direction while an axial force, either toward or away from a patient is applied. The utility of the invention of the subject Patent Application is further enhanced by the formation of a grip portion on the cannula hub and the inclusion of a luer-type coupling system with the cannula hub.

SUMMARY OF THE INVENTION

A universal biopsy system is provided. The universal biopsy system includes a cannula having an open axially extended passage formed therein. The cannula has a distal end with a predetermined contour for penetrating a patient's tissue. The universal biopsy system further includes a cannula hub member having a distal end coupled to a proximal end of the cannula. The hub member has a through bore disposed in axially aligned relationship with the passage of the cannula. Still further, the universal biopsy system includes a handle having an opening formed in a lower side thereof for receiving the cannula hub member therein and releasably engagement therewith.

BRIEF DESCRIPTION OF THE DRAWINGS

FIG. 1A is a cross-sectional view of a portion of the present invention taken along the Section Line 1a—1a of FIG. 1;

FIG. 3 is an exploded perspective view of another embodiment of the present invention; and, FIG. 4 is an enlarged view of a distal end portion of the embodiment of the present invention shown in FIG. 3.

DESCRIPTION OF THE PREFERRED EMBODIMENTS

Figure 1:
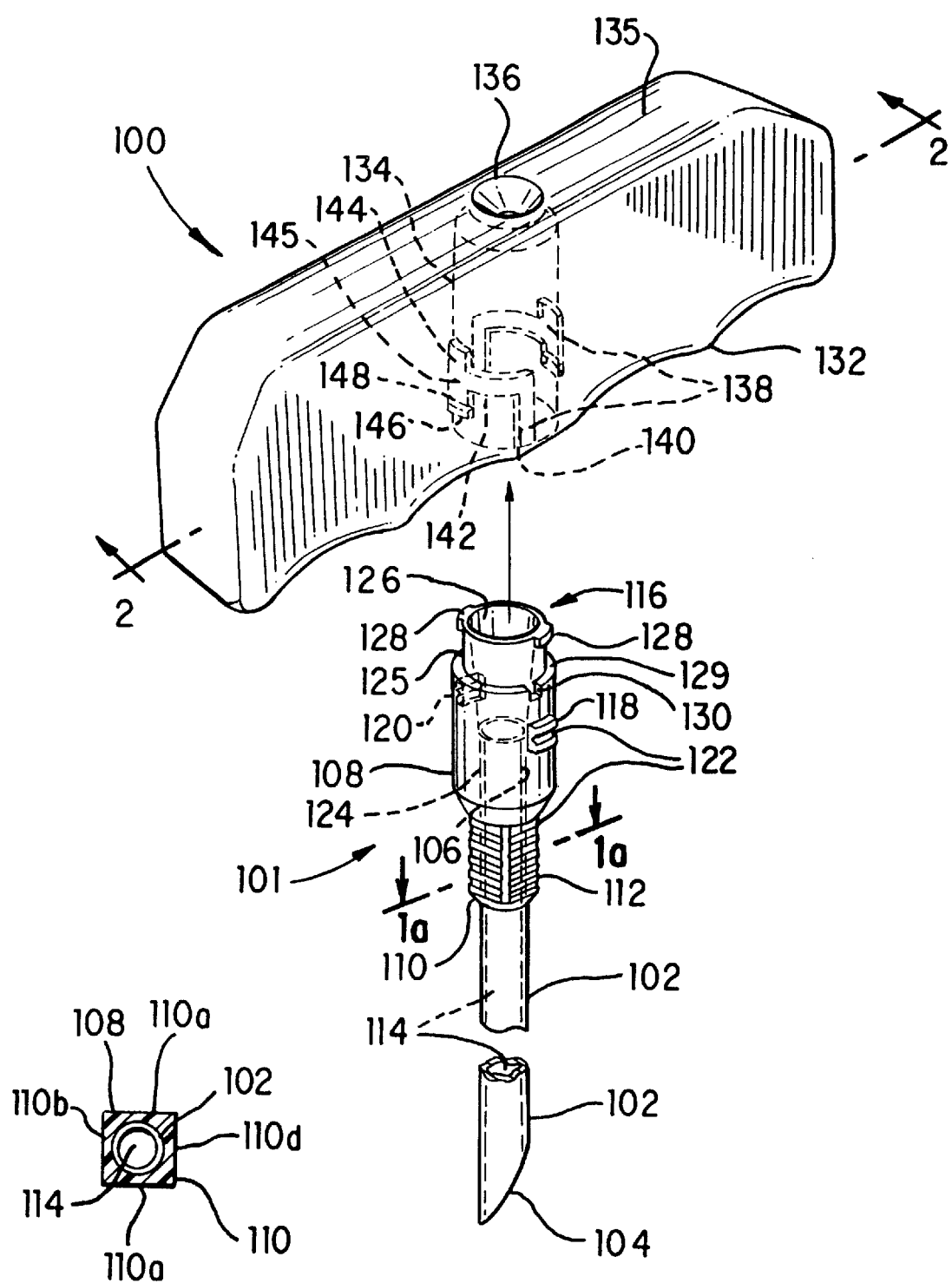
FIG. 1 is an exploded perspective view of the present invention.
Figure 2:
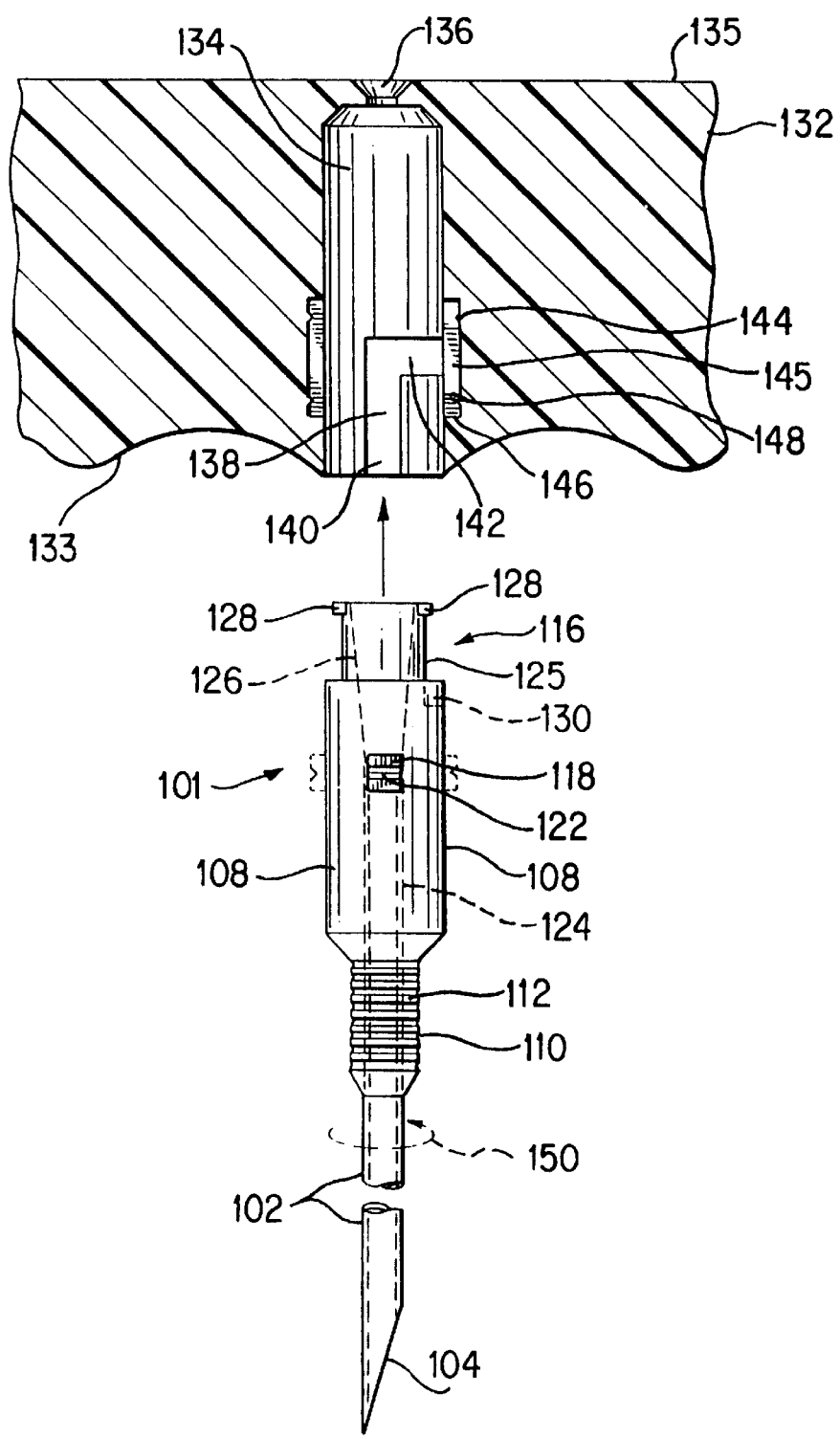
FIG. 2 is a partially sectioned exploded view of the present invention.

Referring to FIGS. 1, 1A and 2, there is shown universal biopsy system 100 for percutaneous medical procedures. As will be seen in following paragraphs, universal biopsy system 100 is specifically directed to the concept of providing a cannula assembly 101 removably coupled to a handle 132, wherein a physician is able to rotate the handle and cannula assembly as an insertion or withdrawing force is applied thereto. Although the universal biopsy system 100 is usable for performing biopsies of both soft tissue and bone, universal biopsy system 100 is particularly adapted for use in performing vertebroplasty and delivery of medicaments. Such applications are facilitated by the removability of the handle 132 from the cannula assembly 101, while still maintaining an ability to rotate the cannula assembly 101 while applying an axially directed force, either to advance the cannula tube 102 or withdraw it.

The cannula assembly 101 includes a cannula tube 102 that is coupled on a proximal end 106 thereof to a cannula hub 108. The cannula tube 102 is formed with an axially extended passageway 114 through which other devices or materials can be passed from a location external to a patient's body to a particular internal site. The distal end 104 of the cannula tube 102 is sharpened to penetrate a patient's bodily structures. The precise configuration of the sharpened end 104 will depend on the particular procedure for which it is to be utilized, and may be configured for coring or cutting when rotated in a particular direction, i.e. clockwise or counterclockwise.

The cannula hub 108 has a grip portion 110 disposed adjacent the distal end of the cannula hub 108. The grip portion 110 has a polygonal contour so that it may be digitally grasped by the physician or engaged with a tool, for supporting the cannula assembly as the handle is removed or installed, and for adjusting the position of the cannula tube 102 subsequent to removal of the handle 132. As particularly shown in the cross-sectional view of FIG. 1A, the grip portion 110 has a substantially square cross-sectional contour having sides 110a–110d. Although a square cross-sectional contour is shown in the drawings, it should be understood by those skilled in the art that other configurations would provide similar functionality, i.e. oval, triangular, pentagonal, hexagonal, octagonal, etc. With appropriate surface treatment, even a circular cross-sectional contour could function to permit the physician to easily displace the cannula tube 102 by displacement of the grip portion 110 of cannula hub 108. Each side 110*a*–110*d* of the grip portion 110 has a plurality of ridges formed thereon for enhancing engagement with the physician's fingers. As shown, the ridges 112 extend horizontally and are disposed in axially displaced parallel relationship. Obviously, other configurations of ridges, such as axially extended ridges which are spaced longitudinally one from another or angularly directed ridges would function similarly. Besides the use of ridges, other methods of enhancing the friction which can be achieved between the surface of the grip portion 110 and the user's fingers may be utilized, such as various forms of knurling or crosscutting.

The proximal end of the cannula hub 108 includes a luer-type coupling system for coupling to other medical devices, such as an aspiration system, a hypodermic syringe, or other medical fluid or semi-fluid delivery systems.

The handle 132 has a bottom or lower surface 133 in which an opening 134 is formed. The opening 134 is dimensioned to receive a proximal portion of the cannula hub 108 therein, and is particularly adapted for releasable coupling therewith. Handle 132 includes a pair of recesses 138 formed in opposing interior wall surfaces of the opening 134 for respectively receiving projections 118, 120 formed on opposing sides of the cannula hub 108. Each of the recesses 138 includes an axially directed section 140 extending from a first end thereof disposed at a distal end of the opening 134, and a circumferential section 142 extending from a second end of the axially directed section to a terminal portion 145 thereof. The terminal portion 145 of each recess 138 extends axially to an upper locking recess 144 and a lower locking recess 146, disposed in axially aligned relationship.

Thus, when the proximal portion of the cannula hub 108 is inserted into the opening 134 the projections 118, 120 slide into a respective recess 138. Each projection 118, 120 is displaced axially through a respective axially directed section 140 of recess 138 until the circumferential section 142 is reached. The physician, utilizing the grip portion 110 of cannula hub 108 then rotates the cannula hub relative to the handle 132, or vice versa, to displace the respective projections 118, 120 along a respective circumferential section 142 of recess 138, as indicated by the directional arrow 150, shown in FIG. 2. If the physician is inserting the cannula tube 102 into a patient's body, the axially directed force applied to the handle 132 would be in a downward direction, toward the distal sharpened end 104 of the cannula tube 102. In that situation, the projections 118, 120 will be received within a respective upper locking recess 144, allowing the physician to rotate the handle in either a clockwise or counterclockwise direction, which rotation is transferred to the cannula assembly 101, while applying a downward force.

If the physician is applying an axial force to the handle for displacing the cannula tube 102 in a direction to at least partially withdraw the cannula tube 102 from the patient, the projections 118, 120 are then received in a respective lower locking recess 146 of the terminal portion 145 of a respective recess 138. With the projections 118, 120 received within a respective lower locking recess 146, the physician is able to rotate the cannula assembly 101 by rotation of the handle 132, while applying an axially directed force in a direction away from the patient.

Proper positioning of the cannula tube 102 may require axial displacement of the cannula tube 102 in a direction toward the patient followed by at least a partial withdrawal, displacing the cannula tube 102 in an opposing direction. Once the cannula assembly 101 has been properly positioned, the handle 132 can be rotated relative to the cannula assembly 101 to position the projections 118, 120 at the end of the axially directed section 140 of a respective recess 138. The handle 132 is then displaced axially with respect to the cannula assembly 101 in order to separate the handle 132 from cannula assembly 101. With the handle removed, the luer-type coupling 116 may then be engaged, or other instruments may be inserted through the through bore 124 of the cannula hub 108 and through the cannula passage 114. Free and clear access to the luer-type coupling 116 and a less obtrusive field of view are of particular importance to the use of biopsy system 100 in providing percutaneous access for other devices and delivering medications or other compositions, such as those compositions utilized in vertebroplasty bone augmentation procedures. Such access and improved field of view are achieved by the removability of handle 132 from the cannula assembly 101.

The luer-type coupling 116 includes a cylindrical body 125 having a diameter less than the diameter of the remaining portion of cannula hub 108. The proximal end 126 of the through bore 124 extending axially through cannula hub 108 has a conically shaped contour, typical of known luer-type couplings, to provide sealing engagement with mating medical couplings and syringes. The proximal end of the cylindrical body 125 has a pair of opposing tabs 128 extending therefrom for engagement with a releasable locking structure of the mating luer-type coupling or syringes. The dimension between the outer extent of the two opposed tabs 128 is no greater than the largest diameter portion of the portion of cannula hub 108 that is received within the opening 134 of handle 132, so that the coupling 116 can be received into the opening 134.

Formed within each lower locking recess 146 there is a latching tab 148 extending therein. Further, each of the projections 118, 120 has a latching groove 122 formed therein for engagement by a respective latching tab 148. Thus, when the handle 132 is pulled relative to the cannula assembly 101 and the projections 118, 120 are received within respective lower locking recesses 146, the handle 132 is maintained in that distended position by the detent action of the latching tabs 148 releasably engaging the grooves 122. The latching tabs respectively engage the latching grooves 122 so that the handle 132 will not be axially displaced relative to the cannula assembly 101 by its own weight. By preventing the handle from "falling" from its uppermost position to its lowermost position, any displacement of the cannula tube 102 which could result from the impact of such a displacement, is avoided. Although latching tabs 148 have been discussed with respect to the lower locking recesses 146, it should be understood that latching tabs may also be formed in the upper locking recesses 144.

Handle 132 has an upper surface 135 having an aperture 136 formed therein. The aperture 136 has a funnel shape and is in open communication with the opening 134 and thereby in open communication with the cannula passage 114. The funnel-shaped aperture 136 provides an access for a guide wire to be passed through the handle 132 and cannula assembly 101. The guide wire is inserted into a patient and the biopsy system 100 is then displaced along the guide wire to accurately locate the cannula tube 102 at a predetermined site within the patient's body.

Cannula hub 108 includes a recess 130 formed in an annular flange 129 disposed adjacent a lower end of the cylindrical luer-type coupling body 125. Recess 130 is provided to receive a projection extending from a medical device, such as a stylette, that is inserted into the cannula passage 114, to prevent relative rotation therebetween.

Referring to FIGS. 3 and 4, there is shown universal biopsy system 100' which incorporates the handle 132, as previously described, and a cannula assembly 101'. The cannula assembly 101' includes a cannula tube 102 coupled to a cannula hub 108, as previously described, and a stylette 160 having a rod-shaped body 162 which is inserted into the passage 114 of cannula tube 102 through the bore 124 of the cannula hub 108. The distal end 168 of the rod-shaped body 162 is shaped for cooperation with the sharpened distal end 104 of cannula tube 102. The shapes of the distal ends 104 and 168 of the cannula tube 102 and rod-shaped body 162, respectively, vary as a function of the procedure for which they are intended to be used. In some cases, the distal end 168 of the stylette rod-shaped body 162 will extend beyond the distal end 104 of the cannula tube 102, and in other cases, the distal ends 104, 168 will be substantially co-located. Further, in some cases, the angles of the sharpened distal ends 104 and 168 will be identical, while in other cases they will differ in order to perform a particular cutting operation.

The proximal end of the rod-shaped body 162 is coupled to a stylette hub 164, the stylette hub 164 being designed to overlay the cylindrical body 125 of the luer-type coupling system 116. The outside diameter of the stylette hub 164 is no greater than the portion of the cannula hub 108 which is inserted into the opening 134 of handle 132. By that arrangement, a stylette 160 can be assembled to the cannula hub 108 and that combination received within the opening of handle 132. Stylette hub 164 includes a projection 166 extending downwardly therefrom for receipt within the recess 130 formed in an annular flange 129 of cannula hub 108, thereby preventing relative rotational displacement of the rod-shaped body 162 relative to the cannula tube 102. The opening 134 in handle 132 is dimensioned to receive a portion of cannula hub 108 with the stylette hub 164 overlying the proximal end, the luer-type coupling 116, and thereby preventing axial displacement of the stylette 160. Thus, when engaged with the handle 132, both the cannula tube 102 and the rod-shaped stylette body 162 are rotated and axially displaced in unison by respective displacement of handle 132, or by respective displacement of the grip portion 110.

The cannula assembly 101', including the stylette 160 is releasably coupled to the handle 132 by means of a pair of projections 118 and 120 that are respectively received within a pair of recesses 138 formed in the handle 132, as previously described. Therefore, subsequent to percutaneous placement, the handle 132 can be removed in order to have access to the stylette 160. For certain procedures, the stylette 160 will be removed and the remaining portion of the cannula assembly 101' utilized for such functions as aspiration, the introduction of medications, the introduction of resinous materials or the introduction of other medical devices.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is being claimed is:

1. A universal biopsy system comprising:
   a cannula having an open axially extended passage formed therein, said cannula having a distal end with a predetermined contour for penetrating a patient's tissue;
   a cannula hub member having a distal end coupled to a proximal end of said cannula and a through bore disposed in axially aligned relationship with said passage of said cannula, said cannula hub member including a pair of projections extending from opposing sides of said cannula hub member; and,
   a handle having an opening formed in a lower side thereof for receiving said cannula hub member therein and releasable engagement therewith. said handle including a pair of recesses formed in opposing interior wall surfaces of said opening for respectively receiving said projections therein, each of said pair of recesses including an axially directed section extending from a first end disposed at a distal end of said opening and a circumferential section extending from a second end of said axially directed section to a terminal portion thereof, said terminal portion of each said circumferential section including an upper locking recess and an opposing lower locking recess for selectively respectively receiving said pair of projections therein to rotationally couple said handle to said cannula hub member responsive an axial displacement of said handle relative to said cannula hub member.

2. The universal biopsy system as recited in claim 1, wherein each of said pair of projections has a latching groove formed therein.

3. The universal biopsy system as recited in claim 2, wherein at least one of said upper and lower locking recesses has a latching tab formed therein for releasable engagement with said latching groove of a respective one of said pair of projections to releasably secure said handle in an axial position relative to said cannula hub member.

4. The universal biopsy system as recited in claim 1, wherein said cannula hub member has a grip portion defined by a distal portion of said cannula hub member having a polygonal outer surface contour.

5. The universal biopsy system as recited in claim 4, wherein said grip portion has a substantially square cross-sectional contour.

6. The universal biopsy system as recited in claim 4, wherein said grip portion has non-planar surfaces formed thereon to enhance a user's ability to grip said grip portion.

7. A universal biopsy system, comprising:
   a cannula having an open axially extending passage formed therein, said cannula having a sharpened distal end;
   a cannula hub member having a distal end coupled to a proximal end of said cannula and a through bore disposed in axially aligned relationship with said passage of said cannula, said cannula hub member including a grip portion defined by a distal portion of said cannula hub member having a polygonal outer surface contour for selective engagement with a tool or a user's fingers, each surface of said polygonal contour having a plurality of ridges formed thereon for enhancing the engagement with the user's fingers;
   a stylette slidably disposed in said through bore of said cannula hub member and said passage of said cannula and having a sharpened distal end corresponding to said sharpened distal end of said cannula; and a handle having an opening formed therein for releasable coupling to said cannula hub member to apply rotational and axially directed forces to said cannula hub member and said cannula, said cannula hub member includes a pair of projections extending from opposing sides of said cannula hub member and said handle includes a pair of recesses formed in opposing interior wall surfaces of said opening for respectively receiving said projections therein, each of said recesses having a latching tab formed in a portion thereof for releasable engagement with a portion of a respective one of said projections to releasably secure said handle in a predetermined axial position relative to said cannula hub member.

8. A universal biopsy system, comprising:

a cannula having an open axially extended passage formed therein, said cannula having a sharpened distal end;

a cannula hub member having a distal end coupled to a proximal end of said cannula, said cannula hub member having a through bore disposed in axially aligned relationship with said passage of said cannula, said cannula hub member including a pair of projections extending from opposing sides of said cannula hub member;

a stylette slidably disposed in said through bore of said cannula hub member and said passage of said cannula and having a sharpened distal end corresponding to said sharpened distal end of said cannula; and, a handle releasably coupled to said cannula hub member within an opening formed in said handle for applying rotational and axially directed forces to said cannula hub member and said cannula, said handle including a pair of recesses formed in opposing interior wall surfaces of said opening for respectively receiving said projections therein, each of said pair of recesses including an axially directed section extending from a first end disposed at a distal end of said opening and a circumferential section extending from a second end of said axially directed section to a terminal portion thereof, said terminal portion of each said circumferential section including an upper locking recess and an opposing lower locking recess for selectively respectively receiving said pair of projections therein to rotationally couple said handle to said cannula hub member responsive an axial displacement of said handle relative to said cannula hub member.

9. The universal biopsy system as recited in claim 8, wherein each of said pair of projections has a latching groove formed therein.

10. The universal biopsy system as recited in claim 9, wherein at least one of said upper and lower locking recesses has a latching tab formed therein for releasable engagement with said latching groove of a respective one of said pair of projections to releasably secure said handle in an axial position relative to said cannula hub member.

* * * * *